United States Patent [19]

Kuehlein et al.

[11] Patent Number: 4,557,959
[45] Date of Patent: Dec. 10, 1985

[54] MULTILAYER MEDICAL WORKING MEANS

[75] Inventors: Georg Kuehlein, Roeslau; Ernst Gerlach, Rehau, both of Fed. Rep. of Germany

[73] Assignee: Rehau Plastiks AG & Co., Rehau, Fed. Rep. of Germany

[21] Appl. No.: 467,191

[22] Filed: Feb. 15, 1983

[51] Int. Cl.$^4$ ............................................. A61M 25/00
[52] U.S. Cl. ....................................... 428/36; 604/408; 604/410; 428/35; 428/518; 428/520; 428/522
[58] Field of Search ................... 604/408, 410; 428/35, 428/36, 518, 520, 522

[56] References Cited

U.S. PATENT DOCUMENTS

| | | | |
|---|---|---|---|
| 2,702,034 | 2/1955 | Walter | 604/408 X |
| 3,298,597 | 1/1967 | Bellamy, Jr. | 604/408 X |
| 3,434,869 | 3/1969 | Davidson | 117/94 |
| 3,618,614 | 11/1971 | Flynn | 128/348 |
| 4,119,267 | 10/1978 | Kydonieus | 604/408 X |
| 4,131,200 | 12/1978 | Rinfret | 604/410 X |
| 4,221,841 | 9/1980 | Hisazumi et al. | 428/518 |
| 4,265,276 | 5/1981 | Hatada et al. | 428/36 X |
| 4,283,447 | 8/1981 | Flynn | 428/36 X |
| 4,337,768 | 7/1982 | Hatada et al. | 604/408 |

FOREIGN PATENT DOCUMENTS 1491682 2/1971 Fed. Rep. of Germany .
2622502 11/1977 Fed. Rep. of Germany .

OTHER PUBLICATIONS

Committe Document by Council of Europe, PA/P-H/Exp.3/T (80) 2COM, Apr. 25, 1980, pp. 11-22.

*Primary Examiner*—George F. Lesmes
*Assistant Examiner*—Nancy A. B. Swisher
*Attorney, Agent, or Firm*—Spencer & Frank

[57] ABSTRACT

A multilayer medical working means comprises at least two walls each made of a glass-clear, soft plastic, with one of the two walls being physiologically unobjectionable and the other wall or walls being a physiologically questionable wall provided with at least one physiologically questionable and/or untested additive. A full-area circumferential connection exists between the physiologically unobjectionable wall and the physiologically questionable wall. A softener gradient is provided between the walls of the working means in such a manner that the physiologically unobjectionable wall has a higher softener content than the physiologically questionable wall directly adjacent thereto which contains at least one physiologically questionable and/or untested additive. The position of the additive is kept constant in the adjacent physiologically questionable wall against the gradient pressure of the softener.

7 Claims, No Drawings

MULTILAYER MEDICAL WORKING MEANS

BACKGROUND OF THE INVENTION

The present invention relates to multilayer medical working means, such as flexible tubes, containers, molded parts, etc., having at least two walls made of a glass-clear, soft plastic, one of the walls being toxicologically unobjectionable and the other wall or walls being provided with additives. A full-area circumferential connection exists between each of the walls.

In the medical field, standards exist which govern whether it is permissable to use a particular plastic in a medical working means. An example of such a standard is German Industrial Standard DIN 58,361, entitled "Transfusionsbehältnisse und Zubehör", in translation, Transfusion Vessels and Accessories". In Europe, the draft PA/PH/Exp. 3/T (80) 3 of the European Pharmacopoeia Commission corresponds to this standard. It provides that technical working means made of plastic are permissible in the medical field, inter alia, only if they are toxicologically unobjectionable and contain neither antioxidants nor coloring agents.

In this connection, the use of softened polyvinyl chloride containing the softener di-(2-ethyl hexyl)-phthalate (DOP) is permissible.

To meet the high demands placed on the use of plastics for the manufacture of medical working means, processes have become known which are intended to prevent the toxicological effect of a certain plastic, which plastic appears to be particularly suitable for the intended type of use, by coating it with other toxicologically unobjectionable plastics. For example, German Pat. No. 1,930,136 discloses a coated catheter which is basically a tube made of rubber or some other elastomer which is provided with a coating of a hydrophilic acrylate or methacrylate, respectively.

After the catheter has begun to swell, the acrylate or methacrylate layer is polymerized to form a solid coating. Antibiotic or germicidal substances can be applied to this layer which are then retained by the hydrophilic coating. Thus, the catheter is made more patient compatible in situ.

Finally, U.S. Pat. No. 3,618,614 discloses a medical tubing comprising a relatively thick, transparent inner tube and a relatively thin, transparent outer tube, each made of plastic. The outer tube is provided with a radiopaque material so that the path of the tube within the patient can be observed on the X-ray screen. The tubing combination disclosed in this patent comprises, for example, an inner tube of polyethylene with additives such as bismuth oxychloride and ethyl-2-(3 amino-2,4,6-triiodobenzoyloxy)butanoate, and an outer tube of polyethylene with additives of triiodo and tetraiodo benzoic acid ester which are distributed homogeneously in the walls of the outer tube as the radiopaque material.

Under consideration of DIN No. 58,361, this tube cannot be used as medical tubing because nonpermissible additives were used together with the basic polymers.

The drawbacks of the prior art in the manufacture of toxicologically unobjectionable working means for medical use are that manufacturing processes are employed for this purpose which are complicated and work-intensive. For example, after extrusion of the basic tubing, the toxicologically unobjectionable layers are applied by a further process step such as immersion, spraying or coating in some other way. When softener-containing PVC materials are used to manufacture the tubing, the tendency of the softener to migrate has in the past not been considered and this migration may lead to the tube walls becoming brittle.

In the past, scant consideration has been given in the medical field to technological working means, for example tube systems, for photosensitive solutions. Contrary to the rules set by DIN No. 58,361, interested consumers have made do with the use of tube systems that were dyed black or dark and with accessories which, although they protected the substance flowing through the tubing against the entire wavelength range of visible as well as invisible light, have the drawback, in addition to the fact that they are used contrary to the standard, that the material flowing through them cannot be observed. Possibly occurring bubble formation, dirt particles or other malfunctions, which have a life threatening importance for the patient, for example during infusions, cannot be observed directly with such working means and can therefore not be alleviated as soon as they occur.

SUMMARY OF THE INVENTION

A primary objeact of the present invention is to provide an improved medical working means which contains a physiologically unobjectionable wall.

Another object of the present invention is to provide a medical working means as, for example, plastic tubing through which a photosensitive material can be conducted without the material being damaged either by the lightwaves or by toxicologically harmful additives and wherein, moreover, transparency is maintained so as to assure observation of the material flowing through the tubing in every phase of its flow.

It is further important object of the present invention to provide such a working means in which the above positive characteristics remain in effect for a longer period of time and are not cancelled out or interfered with, for example, by softener migration.

Additional objects and advantages of the present invention will be set forth in part in the description which follows and in part will be obvious from the description or can be learned by practice of the invention. The objects and advantages are achieved by means of the products, articles, instrumentalities and combinations particularly pointed out in the appended claims.

To achieve the foregoing objects and in accordance with its purpose, the present invention provides a multilayer medical working means, comprising at least two walls each made of a glass-clear, soft plastic, with one of the two walls being physiologicaly unobjectionable and the other wall or walls being a physiologically questionable wall provided with at least one physiologically questionable and/or untested additive, with a full-area circumferential connection existing between the physiologically unobjectionable wall and the physiologically questionable wall which is adjacent to the physiologically unobjectable wall, comprising: a softener gradient between the walls of the working means, with the physiologically unobjectionable wall having a higher softener content than the physiologically questionable wall directly adjacent thereto, which contains the at least one physiologically questionable and/or untested additive, the position of the additive in the adjacent physiologically questionable wall being kept constant in the adjacent physiologically questionable wall against the gradient pressure of the softener.

Preferably, when a softener-containing polyvinyl chloride is used for both the physiologically unobjectionable wall and the physiologically questionable wall, it has been found to be of advantage for the softener gradient between the wall regions of the physiologically unobjectionable wall and the physiologically questionable wall to be in a ratio of 1.1:1 to 9:1.

If in a medical working means according to the present invention, only one wall is made of a soft set polyvinyl chloride, while the other wall or walls are made of other soft polymers, it has been found to be advisable for the softener content of the soft polyvinyl chloride wall to be at least 7 percent by weight.

It is to be understood that both the foregoing general description and the following detailed description are exemplary and explanatory, but are not restrictive of the invention.

DETAILED DESCRIPTION OF THE INVENTION

Preferably in the practice of the present invention the physiologically unobjectionable wall is comprised of soft set polyvinyl chloride. Other suitable polymers that can be used for the physiologically unobjectionable wall are, for example, ethylene-vinyl acetate, vinyl chloride vinyl acetate copolymers, and silicones. For the physiologically unobjectionable inner wall, a composition of for example:

80 parts PVC
20 parts EVA (ethylene-vinyl acetate containing 48 percent vinyl acetate)
10–30 parts softener
2 parts of Ca/Zn stabilizer or
70 parts PVC
30 parts PVCA (vinyl chloride vinyl-acetate copolymer)
10–30 parts softener
2 parts Ca/Zn stabilizer can be used.

When walls of soft set polyvinyl chloride are used for both the physiologically unobjectionable wall and the physiologically questionable wall, the weight percentages for a ratio of 1.1:1 are approximately 8:7, while the weight percentage at the upper limit for a ratio of 9:1 is 63:7. The minimum weight percent proportion of softener in the polyvinyl chloride should be a proportion of 7 weight percent beginning with which the term "polyvinyl chloride soft" begins to be applicable. The upper limit is at 63 weight percent since beginning with this value the polyvinyl chloride begins to become sticky.

If walls made of other polymers are associated with a wall of softened polyvinyl chloride, the minimum weight percent proportion of softener in the polyvinyl chloride must likewise be 7 and the maximum proportion 63.

In the practice of the present invention, the physiologically questionable and/or untested additive may be one or more radiation absorbing substances. The radiation absorbing substance can be one which absorbs radiation in the wavelength range of visible light, just as well as radiation in the wavelength range of invisible light. By selecting specific absorber substances, it is also possible to separately filter out individual radiation ranges of the visible light. Moreover, absorber substances which absorb X-ray radiation can be used as additives.

If a tube structure is used which includes a soft set polyvinyl chloride according to the present invention, this multilayer tube structure having the softener gradient according to the present invention between two adjacent wall regions can be used, for example, for the observable transport of photosensitive flowing materials. The softener gradient according to the present invention between the two adjacent tube walls produces an osmosis-like state when one wall region is stressed with softener components to a greater extent than the other wall region. The increased softener components in the one wall region then slowly move, by way of unilateral diffusion, into the adjacent wall region having the lower softener proportion in a desire to equalize the existing softener gradient. Thus, according to the present invention, a softener pressure differential, so to speak, is created between adjacent wall regions so that, on the basis of the larger proportions in the one wall, there is a tendency toward osmotic or pressure differential equalization with respect to the other wall.

This tendency to equalize the pressure on the part of the softener components is counteracted by the tendency to migrate on the part of the additives in the wall region containing less softener components, and these additives, due to the complete absence of such components in the tube wall containing the larger proportion of softeners, exhibit the reverse osmotic equalization tendency.

However, the migratory tendency of these additives, which are, for example, UV absorbers, e.g. derivatives of benzophenone, substituted benzotriazoles, organic metal complexes, particularly of nickel, cinnamic acid derivatives and other commercially available transparent pigments or dyes, or transparent X-ray contrast furnishing substances such as ethyl-2(3 amino-2,4,6-triiodobenzoyloxy)butanoate, is counteracted by the pressure of the softener substances so that migration of molecules of these additives from the wall region containing less softener into the wall region containing the greater amount of softener is prevented.

However, such additives may also be cross-linking media, such as peroxides, or cross-linking aids, such as radiation activators. When the cross-linking is completed, physiologically objectionable residues remain in the tube walls. Cross-linking may take place here by way of energy absorption by means of radiation or by chemical means. Although when employing radiation cross-linking, the addition of cross-linking activators can reduce the high dosage of normal radiation cross-linking, and thus reduce the partial material decomposition due to radiation which may lead to the formation of toxic decay products, reduced formation of such toxic decay products can also not be excluded even if cross-linking activators are added. Chemical cross-linking in any case involves considerable residues in the walls of the cross-linked plastic member. These residues can be neutralized in situ by the softener gradient according to the present invention. The cross-linking may also result in an improvement of bending resistance, optimization of the resetting capability and reduction of cold flow in prefabricated parts such as infusion/transfusion implements.

The gradient pressure of the softener from wall region to wall region may be built up in such a manner that, even theoretically, pressure equalization in such medical working means is impossible during the storage period permitted for such working means according to pharmaceutics legislation. At temperatures up to 23° C. the storage period should not exceed 12 months.

If such medical working means are used with a wall structure in which, for example, the physiologically unobjectionable wall is made of a soft set polyvinyl chloride, and the adjacent wall is made of another soft polymer without softener components, the same behavior as described above results for the penetration of the softener from the one wall into the softener-free polymer wall. In this case, the softener content of the polyvinyl chloride wall can be set to correspond to the specific requirements for the adjacent wall of softener free polymer.

According to the present invention, the rule applies that the greater the softener gradient from the one wall to the other wall, the longer the gradient acts in the sense of the invention, and the longer the penetration of physiologically questionable and/or untested components from the one wall into the physiologically unobjectionably set other wall is prevented. However, it also applies that the maximum limit of the softener component charge in the polyvinyl chloride is at 63 weight percent.

The principle according to the present invention can be used in connection with tubing produced, for example, in a coextrusion process as two or multiple layer structures. Other process techniques for the production of multilayer tubing are of course covered as well. The same applies for other medical working means, such as infusion bags, molded parts for tube connections, containers, molded member etc. In this respect, care should always be take that a homogeneous layer termination exists between the wall portion containing the softener or having the higher softener content and the wall portion containing less or no softener at all, so that the blocking effect against migration of physiologically questionable and/or untested additives with respect to the material to be transported or conducted remains in effect. The connections between the various wall portions in a multilayer wall structure of such a medical working means can be effected, for example, by welding, gluing, by way of coextrusion, etc., which thus forms a laminated structure.

A softener to be used for the wall regions made of polyvinyl chloride may be, for example, the di-(2-ethyl hexyl)-phthalate (DOP) permitted by DIN 58,361. However, other softeners, such as dioctyl adipates or polymer softeners based on adipic acid can also be used. The important factor in this connection is the appropriate adaptation to the material to be conducted or transported, so as to substantially prevent washouts. Such washouts may reduce the softener components in the one wall and thus negatively influence the pressure buildup between adjacent wall regions. This could be the case particularly where, according to the present invention, tubing is designed in such a way that its inner walls consist of a physiologically unobjectionable soft polyvinyl chloride which is surrounded by an outer wall made of physiologically questionable and/or untested additives.

In addition to the softener gradient according to the present invention between adjacent wall regions, a further preferred feature of the present invention is the use of absorber substances in wall regions of a medical working means made of plastic where these absorber substances filter out, according to the present invention, parts of the visible and/or invisible light without negatively influencing the transparency of the multilayer structure of the working means. According to the present invention, the wavelength ranges to be covered in the invisible and visible light should be between 220 and 750 nanometers. The reason for this is the photosensitivity of the material being conducted or transported, which, if there is no protection, would result either in photochemical decomposition or in oxidative decomposition with energy as the catalyst due to activation in a certain wavelength range.

In addition to the above-mentioned nanometer ranges, the X-ray range from 0.01 to 50 nanometers can also be covered by suitable additives. In individual cases, various absorber additives make it possible to cover every wavelength range of visible light and still meet the requirement made by the present invention of maintaining the transparency necessary for observation of the material being conducted or transported. The same applies for the stated wavelength ranges of invisible light as well as the stated x-ray ranges.

The following examples are given by way of illustration to further explain the principles of the invention. These examples are merely illustrative and are not to be understood as limiting the scope and underlying principles of the invention in any way. All percentages referred to herein are by weight unless otherwise indicated.

EXAMPLE 1

A composite tubing is produced having an inner diameter of 4.5 mm and a wall thickness of 1.35 mm. The composite tubing comprises an inner tubing which is physiologically unobjectionable and a jacket tubing which is physiologically questionable and which surrounds the inner tubing.

The following components were used for the composition of the jacket tube:
100 parts S-PVC
16 parts softener
2 parts calcium/zinc stabilizer (Ca/Zn)
5 parts epoxidized soy bean oil
0.06 part Euvenyl blue of BASF, Ludwigshafen, W. Germany
0.02 part Cyasorb UV 24 of American Cyanamid Comp., Wayne N.J.

The tubing material made from this composition filters 100% of the light in wavelengths between 220 and 376 nm. The visible light is covered over a range from 350 to 376 nm and the ultraviolet range from 220 to 350 nm. Due to the added additives, namely the Euvenyl blue and Cyasorb UV 24, the jacket tube is physiologically questionable. The layer thickness of the jacket tube is 0.7 mm.

The following components were used for the composition of the inner tubing:
100 parts S-PVC
50 parts softener
2 parts Ca/Zn stabilizer
5 parts epoxidized soy bean oil The layer thickness of this inner tubing is 0.65 mm. Due to its additives, it can be called physiologically unobjectionable.

The composite tubing of this example can be used to conduct materials which are sensitive to the stated wavelength ranges of visible and invisible light. These ranges can be varied by replacing the Euvenyl blue of the example by any other desired dyestuffs. The following palette, for example, may be considered:

Irgazin  nm ranges from 380 to 510

-continued

| | | |
|---|---|---|
| yellow Irgazin orange | nm ranges from 380 to 540 | |
| Irgazin red | nm ranges from 450 to 570 | of Ciba Geigy A Basel, Switzerland |
| Irgazin violet | nm ranges from 520 to 560 | |
| Irgazin blue | nm ranges from 580 to 750 | |

One or a plurality of these dyestuffs can be used individually or in combinations with one another.

EXAMPLE 2

A composite tubing is produced having an inner diameter of 4.5 mm and a wall thickness of 1.35 mm. The composite tubing comprises an inner tubing, a center tubing covering the inner tubing, and an outer tubing covering the center tubing.

The composition for the inner tube includes the following components:
100 parts S-PVC
50 parts softener
2 parts Ca/Zn stabilizer
5 parts epoxidized soy bean oil This inner tubing has a layer thickness of 0.4 mm. Due to its components, it can be called physiologically unobjectionable.

In a coextrusion process, the center tubing is extruded onto the inner tubing and has to the following composition:
100 parts S-PVC
15 parts softener
2 parts Ca/Zn stabilizer
5 parts epoxidized soy bean oil
0.2 part Cyasorb UV 24

This center tube jacket filters 100% of the wavelengths between 220 and 350 nm and, because of its additives, is considered physiologically questionable.

In a coextrusion process, the center tubing hose is likewise provided with an outer tubing which has the following composition:
100 parts S-PVC
50 parts softener
2 parts Ca/Zn stabilizer
5 parts epoxidized soy bean oil The layer thickness of this outer tubing is 0.4 mm. The layer thickness of the center tube is 0.55 mm.

In this Example 2, the outer and inner tubing are set to be physiologically unobjectionable, while the center tubing contains the physiologically questionable substances.

The softener gradient from the inner tubing to the center tubing and from the outer tubing to the center tubing, however, prevents the penetration of dangerous substances from the center tubing toward the interior as well as toward the exterior. The composite tubing of this example can be used for transporting flowable material just as well as, for example, a drainage tube for draining wounds where the outer tubing is in contact with the wound and must be unobjectionable.

EXAMPLE 3

A composite tubing is produced having an inner diameter of 3.0 mm and a wall thickness of 0.55 mm. The composite tubing comprises an outer tubing and an inner tubing.

The outer tubing has the following composition:
100 parts S-PVC
18 parts softener 2 parts Ca/Zn stabilizer
5 parts epoxidized soy bean oil
0.3 part Cyasorb UV 24

This outer tubing has a layer thickness of 0.2 mm and filters 100% of the wavelengths between 220 and 350 nm. On the basis of its components, the tube structure of the outer tubing must be considered to be physiologically questionable.

An inner tube is sprayed into this outer tube to a layer thickness of 0.35 mm and according to the following composition:
100 parts S-PVC
50 parts softener
2 parts Ca/Zn stabilizer
5 parts epoxidized soy bean oil This inner tube is physiologically acceptable as well.

EXAMPLE 4

A composite tubing is manufactured having an inner diameter of 3.0 mm and a wall thickness of 0.55 mm. The composite tubing comprises an inner tubing containing physiologically objectionable components and an outer tubing which is physiologically unobjectional.

The inner tube has the following composition:
100 parts S-PVC
14 parts 2-ethoxyethyl-2,3,4,6-tetra-iodobenzoate
8 parts epoxidized soy bean oil
2 parts Ca/Zn stabilizer The layer thickness of the inner tube is 0.2 mm and, on the basis of its additives, it must be considered physiologically objectionable. The additive 2-ethoxyethyl-2,3,4,6-tetra-iodobenzoate, introduced as an X-ray contrast medium, absorbs X-rays and can therefore be located in the patient's body.

An outer tube is sprayed onto this inner tube and has the following composition:
100 parts S-PVC
50 parts softener
2 parts Ca/Zn stabilizer
8 parts epoxidized soy bean oil This outer tube has a layer thickness of 0.35 mm and is physiologically unobjectionable. The softener gradient according to the present invention becomes noticeable insofar as the larger proportions of softener in the outer tube prevent the penetration of the X-ray contrast medium to the surface of the outer tube. The composite tubing of this example can be used as a wound drainage since its outer skin is physiologically unobjectionable.

EXAMPLE 5

A composite tubing is produced having an inner diameter of 4 mm and a wall thickness of 1 mm. The composite tubing comprises four layers of the following structure:

An outer tube according to the following composition:
100 parts S-PVC
50 parts softener
2 parts Ca/Zn stabilizer
8 parts epoxidized soy bean oil This outer tube has a layer thickness of 0.2 mm and, due to its components, can be considered phyisiologically unobjectionable.

This outer tube is connected to an absorber tube immediately within the outer tube and made according to the following composition:

100 parts S-PVC
18 parts softener
2 parts Ca/Zn stabilizer
8 parts epoxidized soy bean oil
0.3 part Cyasorb UV 24

This absorber tube has a layer thickness of 0.2 mm and, on the basis of its additives, it absorbs wavelengths from 220 to 350 nm in the ultraviolet range, so that the X-ray contrast medium embedded in the next following tube layer underneath the absorber tube is protected against damaging ultraviolet radiation. The absorber tube itself, due to its structure, must be considered physiologically questionable.

A contrast tube according to the following composition is sprayed underneath the absorber tube of this tube structure:

100 parts S-PVC
18 parts softener
15 parts 1,10 diiododecane
2 parts Ca/Zn stabilizer
8 parts epoxidized soy bean oil This contrast tubing has a layer thickness of 0.2 mm and absorbs X-ray radiation, while remaining glass-clear and colorless because the ultraviolet filter ahead of it prevents iodine splitting. On the basis of its additives, the tube structure must be considered physiologically questionable.

Finally, an inner tube according to the following composition is added to the composite tubing beneath the contrast tube:

100 parts S-PVC
50 parts softener
2 parts Ca/Zn stabilizer
8 parts epoxidized soy bean oil The layer thickness of the inner tube is 0.4 mm and it can be considered to be physiologically unobjectionable.

This example points out that multilayer structures are within the scope of the present invention, and that a plurality of tube or hose layers containing physiologically questionable additives can be enclosed in a physiologically unobjectionable setting. The inner tubing layers (absorber tube and contrast tube) containing the physiologically questionable additives may protect one another or may offer unilateral protection, as is the case, for example, with the absorber tube of the present example with respect to the contrast tubing.

EXAMPLE 6

A composite tubing is produced having an inner diameter of 3 mm and a wall thickness of 1 mm. The composite tubing comprises an outer tube and an inner tube.

The outer tube has the following composition:
100 parts polyurethane
0.6 part Euvenyl blue
3 parts Cyasorb UV 24

This outer tube has a layer thickness of 0.4 mm and absorbs 100% of the light between the wavelengths of 220 and 370 nm at 100%. The outer tube is considered physiologically objectionable.

The associated inner tube has a layer thickness of 0.6 mm and has the following composition:
100 parts S-PVC
50 parts softener
2 parts Ca/Zn stabilizer
5 parts epoxidized soy bean oil In contrast to the outer tube, the inner tube is physiologically unobjectionable.

EXAMPLE 7

A composite tubing is made having an inner diameter of 2.5 mm and a wall thickness of 0.75 mm. The composite tubing comprises an outer tube and an inner tube.

The composition for the outer tube correspond to that for the outer tube of Example 2. Its layer thickness is 0.3 mm and the outer tube is physiologically unobjectionable.

This outer tube has an associated inner tube made according to the following composition:
100 parts ethylene vinyl acetate (EVA) containing 12% vinyl acetate
140 parts 1,10 diiododecane
3 parts Cyasorb UV 24

The layer thickness of the inner tube is 0.45%. The inner tube absorbs UV light and additionally furnishes X-ray contrast.

EXAMPLE 8

A composite tubing is produced having an inner diameter of 4 mm and a wall thickness of 1 mm. The composite tubing comprises an outer tube and an inner tube.

The outer tube is made according to the following composition:
100 parts polydimethyl siloxane containing 3% dichlorobenzoyl peroxide
3 parts Cyasorb UV 24.

The layer thickness of the outer tube is 0.2 mm and is applied by dipping. The outer tube absorbs UV light from 220 to 350 nm.

The inner tube is made according to the same composition as the inner tube of Example 1. The layer thickness of the inner tube is 0.8 mm.

Examples 6 to 8 indicate that the present invention can be used effectively in cases where only one layer is made of a softened polyvinyl chloride and the other layer is made of a softener free polymer. The softened polyvinyl chloride tubing layer is the physiologically unobjectionable layer which, with its softener gradient, presses against the components of the softener free polymer tubing which is the physiologically questionable outer covering tube. The softened polyvinyl chloride tubing prevents the transfer of these components from the softener-free polymer tubing through the polyvinyl chloride softener-containing tubing into the material flowing through the composite tubing.

EXAMPLE 9

A physiologically unobjectionable inner tube is provided with a jacket tube which, in addition to other additives, contains a chemical cross-linking agent for a subsequent chemical cross-linking process.

The composition for the inner tube includes the following components:
100 parts S-PVC
50 parts softener
2 parts Ca/Zn stabilizer
5 parts epoxidized soy bean oil The jacket tube of this example is made according to the following composition:
50 parts S-PVC
50 parts ethylene vinyl acetate copolymer containing 60 to 70% vinyl acetate
5 parts Ca/Zn stabilizer 1.5 part stearic acid
10 parts softener
5 parts epoxidized soy bean oil
2 parts 2,2-(tert.butylperoxy)-butane as chemical cross-linking agent Following its manufacture, the outer tube was chemically cross-linked in order to attain the described optimum characteristics.

EXAMPLE 10

A composite tubing is provided comprising an inner tube and an outer tube.

In this Example, the inner tube is made according to the following composition:
100 parts S-PVC
16 parts softener
2 parts Ca/Zn stabilizer
5 parts epoxidized soy bean oil The composition for the outer tube includes the following components:
100 parts ethylene vinyl acetate copolymer
42 parts S-PVC
15 parts softener
3 parts epoxidized soy bean oil
2 parts Ca/Zn stabilizer
3 parts 2,2-(butylperoxy)-butane
1.5 part stearic acid
2 parts triallyl cyanurate as cross-linking aid The outer tube is cross-linked after manufacture.

The two chemical cross-linking aids mentioned in Examples 9 and 10 do not constitute a complete listing of the cross-linking aids which can be used. Any commercially available chemical cross-linking agent can be used here.

EXAMPLE 11

A composite tubing is provided which comprises an inner tube and an outer tube which can be subjected to a subsequent radiation cross-linking process.

The tubing structure is selected as follows:

The inner tube is made according to the following composition:
100 parts S-PVC
16 parts softener
4 parts Ca/Zn stabilizer
6 parts epoxidized soy bean oil The outer tube has the following composition:
50 parts S-PVC
50 parts ethylene vinyl acetate copolymer
5 parts Ca/Zn stabilizer
1.5 part stearic acid
10 parts softener
3 parts triallyl cyanurate The radiation cross-linking here took place with a radiation amounting to 5 Mrd.

It will be understood that the above description of the present invention is susceptible to various modifications, changes and adaptations, and the same are intended to be comprehended within the meaning and range of equivalents of the appended claims.

What is claimed is:

1. Multilayer medical working means for containing or transporting a physiological material, said medical working means comprising at least two walls laminated together, wherein;
   (a) each said wall is made of a glass-clear, soft plastic;
   (b) one of said two walls is physiologically unobjectionable and the other said wall is a physiologically questionable wall provided with at least one of a physiologically questionable and untested additive, wherein said physiologically unobjectionable wall is arranged to be directly adjacent a physiological material contained or transported by said medical working means;
   (c) said two walls are adjacent one another and are connected together by a full-area circumferential connection; and
   (d) said physiologically unobjectionable wall has a higher content of resin softening material than said physiologically questionable wall, causing a softener gradient to be present between said two walls, the position of said additive in said physiologically questionable wall being kept constant in the said physiologically questionable wall against the pressure of the softener gradient.

2. Medical working means as defined in claim 1, wherein a soft set polyvinyl chloride is used for the physiologically unobjectionable wall and for the physiologically questionable wall, and the softener gradient between the physiologically unobjectionable wall and the physiologically questionable wall has a ratio of 1.1 to 1 to 9 to 1.

3. Medical working means as defined in claim 1, wherein the physiologically unobjectionable wall is comprised of soft set polyvinyl chloride and the physiologically questionable wall is comprised of another soft polymer, and the softener proportion in the polyvinyl chloride is at least 7 percent by weight.

4. Medical working means as defined in claim 1, wherein the additive is a radiation absorbing substance.

5. Medical working means as defined in claim 4, wherein the additive absorbs radiation in the wavelength range of visible light.

6. Medical working means as defined in claim 4, wherein the additive absorbs radiation in the wavelength range of invisible light.

7. Medical working means as defined in claim 4, wherein the additive absorbs radiation in the wavelength range of X-ray radiation.

* * * * *